United States Patent [19]

Hewick et al.

[11] Patent Number: 5,322,837

[45] Date of Patent: * Jun. 21, 1994

[54] HOMOGENEOUS ERYTHROPOIETIN COMPOSITIONS AND METHODS OF USING SAME

[75] Inventors: Rodney M. Hewick, Lexington; Jasbir S. Seenra, Arlington, both of Mass.

[73] Assignee: Genetics Institute, Inc., Cambridge, Mass.

[*] Notice: The portion of the term of this patent subsequent to Jun. 30, 2004 has been disclaimed.

[21] Appl. No.: 903,220

[22] Filed: Jul. 31, 1992

Related U.S. Application Data

[63] Continuation of Ser. No. 780,429, Oct. 23, 1991, abandoned, which is a continuation of Ser. No. 328,535, Mar. 24, 1989, abandoned, which is a continuation of Ser. No. 67,021, Jun. 29, 1987, abandoned, which is a continuation of Ser. No. 690,853, Jan. 11, 1985, Pat. No. 4,677,195.

[51] Int. Cl.$^5$ .................. A61K 37/24; C07K 15/14
[52] U.S. Cl. ............................... 514/8; 514/12; 514/21; 530/380; 530/397
[58] Field of Search ............ 530/380, 397, 395; 514/8, 12, 21

[56] References Cited

U.S. PATENT DOCUMENTS

| | | | |
|---|---|---|---|
| 4,289,690 | 9/1981 | Pestka et al. | 530/351 |
| 4,558,005 | 12/1985 | Goldwasser et al. | 424/85.8 |
| 4,568,488 | 2/1986 | Lee-Huang | 424/85.8 |
| 4,677,195 | 1/1987 | Hewick et al. | 530/397 |
| 4,703,008 | 10/1987 | Lin | 435/240.2 |

OTHER PUBLICATIONS

Miyake et al., J. Biol. Chem., 252, 5558–5564 (1977).

*Primary Examiner*—Howard E. Schain
*Attorney, Agent, or Firm*—Bruce M. Eisen; Scott A. Brown; Ellen A. Kapinos

[57] ABSTRACT

A method for purifying erythropoietin is described. The method comprises treating partially purifying erythropoietin by reverse phase high performance liquid chromatography to obtain homogeneous erythropoietin having a molecular weight of about 34,000 daltons on SDS PAGE and moving a single peak on reverse phase HPLC. The homogeneous erythropoietin protein preferably has a specific activity of at least 120,000 IU, more preferably at least 160,000 IU per absorbance unit at 280 nm.

7 Claims, 1 Drawing Sheet

HOMOGENEOUS ERYTHROPOIETIN COMPOSITIONS AND METHODS OF USING SAME

CROSS-REFERENCE TO RELATED APPLICATIONS

This application is a continuation of application Ser. No. 07/780,429, filed Oct. 23, 1991, now abandoned which in turn is a continuation of application Ser. No. 328,535, filed Mar. 24, 1989, now abandoned which is a continuation of application Ser. No. 067,021, filed Jun. 29, 1987, now abandoned which is a continuation of application Ser. No. 690,853, filed Jan. 11, 1985 that issued as U.S. Pat. No. 4,677,195 on Jun. 30, 1987.

FIELD OF THE INVENTION

The present invention is directed to the purification of erythropoietin and to compositions comprising highly purified erythropoietin.

BACKGROUND OF THE INVENTION

Erythropoietin (hereinafter EPO) is a circulating glycoprotein, which stimulates erythrocyte formation in higher organisms. See, Carnot et al., *Compt. Rend.*, 143:384 (1906). As such, EPO is sometimes referred to as an erythropoiesis stimulating factor.

The life of human erythrocytes is about 120 days. Thus, about 1/120 of the total erythrocytes are destroyed daily in the reticulo-endothelial system. Concurrently, a relatively constant number of erythrocytes are produced daily to maintain the level of erythrocytes at all times (Guyton, *Textbook of Medical Physiology*, pp. 56-60, W. B. Saunders Co., Philadelphia (1976)).

Erythrocytes are produced by the maturation and differentiation of the erythroblasts in bone marrow, and EPO is a factor which acts on less differentiated cells and induces their differentiation to erythrocytes (Guyton, supra).

EPO is a promising therapeutic agent for the clinical treatment of anemia or, in particular, renal anemia. Unfortunately, the use of EPO is not yet common in practical therapy due to its low availability.

For EPO to be used as a therapeutic agent, consideration should be given to possible antigenicity problems, and it is therefore preferable that EPO be prepared from a raw material of human origin. For example, human blood or urine from patients suffering from aplastic anemia or like diseases who excrete large amounts of EPO may be employed. These raw materials however, are in limited supply. See, for example, White et al., *Rec. Progr. Horm. Res.*, 16:219 (1960); Espada et al., *Biochem. Med.*, 3:475 (1970); Fisher, *Pharmacol. Rev.*, 24:459 (1972) and Gordon, *Vitam. Horm.* (*N.Y.*) 31:105 (1973), the disclosures of which are incorporated herein by reference.

The preparation of EPO products has generally been via the concentration and purification of urine from patients exhibiting high EPO levels, such as those suffering from aplastic anemia and like diseases. See for example, U.S. Pat. Nos. 4,397,840, 4,303,650 and 3,865,801 the disclosures of which are incorporated herein by reference. The limited supply of such urine is an obstacle to the practical use of EPO, and thus it is highly desirable to prepare EPO products from the urine of healthy humans. A problem in the use of urine from healthy humans is the low content of EPO therein in comparison with that from anemic patients. In addition, the urine of healthy individuals contains certain inhibiting factors which act against erthropoiesis in sufficiently high concentration so that a satisfactory therapeutic effect would be obtained from EPO derived therefrom only following significant purification.

EPO can also be recovered from sheep blood plasma, and the separation of EPO from such blood plasma has provided satisfactorily potent and stable water-soluble preparations. See, Goldwasser, *Control Cellular Dif. Develop.*, Part A; pp 487-494, Alan R. Liss, Inc., N.Y., (1981), which is incorporated herein by reference. Sheep EPO would, however, be expected to be antigenic in humans.

Thus, while EPO is a desirable therapeutic agent, conventional isolation and purification techniques, used which natural supply sources, are inadequate for the mass production of this compound.

Sugimoto et al., in U.S. Pat. No. 4,377,513 describe one method for the mass production of EPO comprising the in vivo multiplications of human lymphoblastoid cells, including Namalwa, BALL-1, NALL-1, TALL-1 and JBL.

For therapeutic use of EPO, it is necessary to purify the EPO protein to homogeneity.

SUMMARY OF THE INVENTION

EPO has been purified from the urine of patients with aplastic anemia by methods described by Miyake et al., *J. Biol. Chem.*, 252:5558 (1977). It had been thought that EPO purified by this method was homogeneous because it moved as a single band during electrophoresus. It has now been discovered that this seemingly homogeneous EPO composition produced by the method of Mayaki et al. is composed of several polypeptide components ranging from 30,000 to 70,000 daltons.

In accord with the present invention a homogeneous EPO protein composition is prepared by treating partially purified EPO by reverse phase high performance liquid chromatography and eluting the EPO protein in preferably an acetonitrile gradient to purify the EPO protein to homogeneity. In accord with this invention pure EPO protein is produced having a molecular weight of about 34,000 daltons on SDS PAGE and moving as a single peak on reverse phase HPLC. The EPO preferably has a specific activity of at least 120,000 international Units (IU) per absorbance unit at 280 nanometers, and more preferably 160,000 IU.

DETAILED DESCRIPTION OF THE INVENTION

Figure 1:
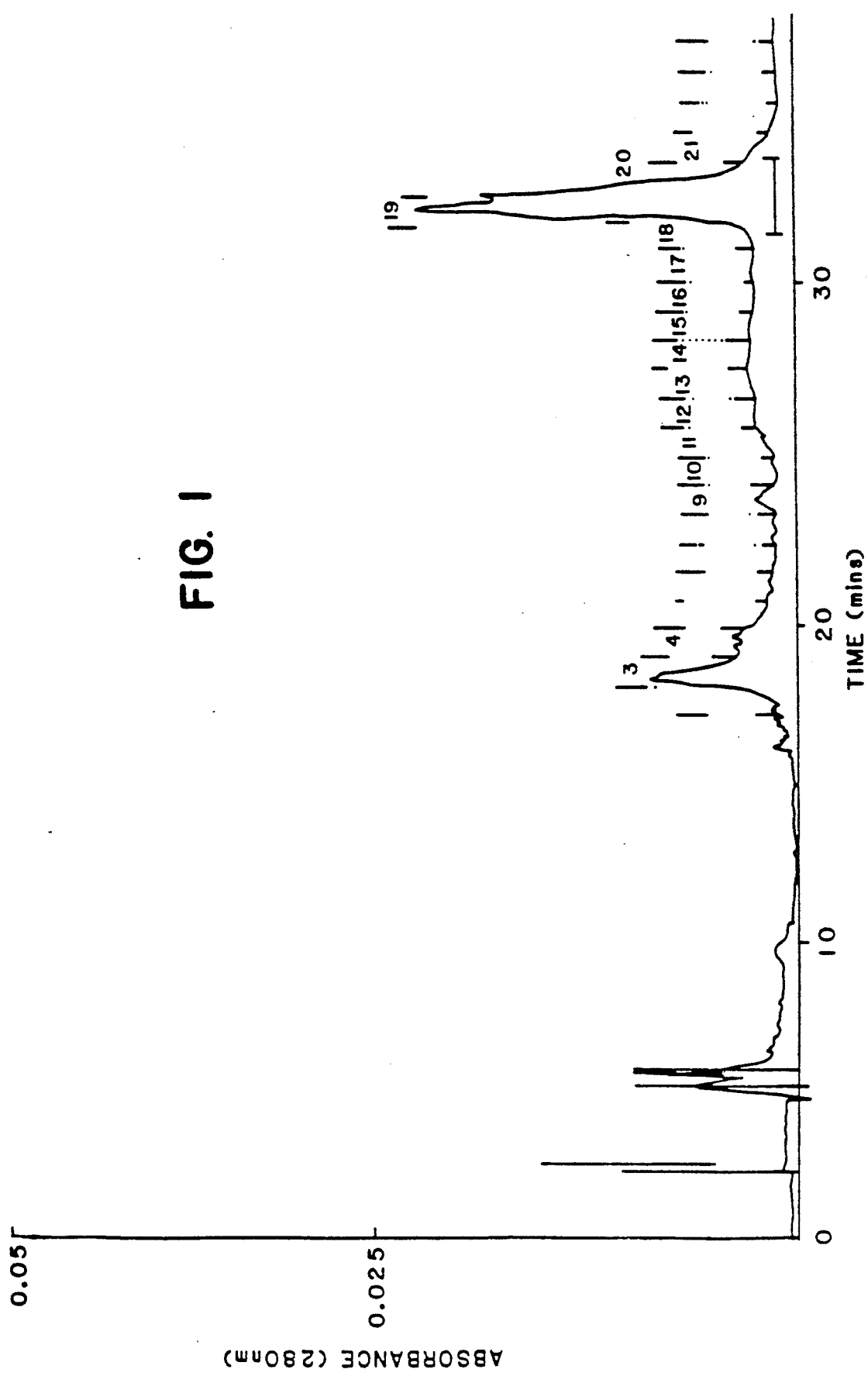
FIG. 1 is an elution profile of an EPO composition treated by reverse phase high performance liquid chromatography in accord with the present invention illustrating absorbance of fractions at 280 nm versus time.

In accord with the present invention, it was found essential to treat purified EPO compositions by reverse phase high performance liquid chromatography in order to obtain homogeneous EPO protein.

EPO can be obtained from several sources which include from the blood or urine or patients suffering from asplastic anemia (natural sources) or from expression of genetically engineered vectors introduced into organisms for production of EPO by cell culture and fermentation processes.

No matter what the source of EPO is, the EPO protein must be purified to homogeneity for therapeutic use. The crude EPO compositions obtained from natural sources or from expression in transformed cells containing genetically engineered DNA vectors can be partially purified by a variety of techniques. Preferably, the method for purifying EPO that was described by Miyake et al. in *J. Biol. Chem.*, 252:5558 (1977) is used. The method of Miyake et al. comprises deactivating any proteolytic enzymes by treating the crude EPO preparations with phenol p-aminosalicylate. Such proteases can also be deactivated by other means such as by heating, which is presently preferred. The purification steps described by Miyake et al. include ethanol precipitation, DEAE-agarose fractionation, sulfopropyl-Sephadex chromatography, gel filtration and hydroxylapatite chromatography. Of course other equivalent procedures could be substituted for the steps of Miyake et al in order to obtain a "purified" EPO composition preferably having a specific EPO activity of at least about 50,000, preferably at least about to 80,000 IU per absorbance unit at 280 nm.

The "purified" EPO composition has been found to be non-homogeneous. Thus, in accord with the present invention, the "purified" EPO composition is further treated by reverse phase high performance liquid chromatography (RPHPLC) to obtain a homogeneous EPO protein composition having a molecular weight of about 34,000 daltons when analyzed by sodium dodecyl sulfate (SDS) polyacrylamide gel electrophoresus (PAGE). Preferably, the reverse phase HPLC is conducted on a C-4 Vydac column using an eluant consisting of a 0 to 95% acetonitrile gradient in 0.01 to 1.0%, preferably 0.1% trifuloroacetic acid over a period of about 100 minutes. Other equivalent combinations of columns and eluants can be used.

When purified in accord with the present invention, EPO compositions having a specific activity of at least 120,000 IU, preferably 160,000 IU, per absorbance unit at 250 nm are obtained.

An "absorbance unit", as used herein, is approximately 1 mg protein per ml.

The amino acid sequence of an EPO protein derived from a human source, including its secretory leader sequence is illustrated in FIG. 2. The mature EPO protein begins with the "Ala" residue identified by the arabic numeral "1". The secretory leader sequence is the polypeptide sequence preceding the mature EPO protein beginning with the "MET" residue identified by the numeral "-27". Typically, the EPO protein having the secretory leader sequence is expressed in a cell capable of processing the protein to eliminate the leader sequence and secrete the mature protein into the media. The mature EPO protein may be expressed by recombinant means without using DNA coding for the secretory leader sequence and, in such case, may have a "Met" residue immediately preceding the "Ala" residue beginning the mature EPO protein (sometimes referred to as Met-EPO).

The biologically active EPO produced from natural sources or by the procaryotic or eucaryotic expression of cloned EPO genes and purified in accord with the present invention can be used for the in vivo treatment of mammalian species by physicians and/or veterinarians. The amount of active ingredient will, of course, depend upon the severity of the condition being treated, the route of administration chosen, and the specific activity of the active EPO, and ultimately will be decided by the attending physician or veterinarian. Such amount of active EPO was determined by the attending physician is also referred to herein as and "EPO treatment effective" amount. For example, in the treatment of induced hypoproliferative anemia associated with chronic renal failure in sheep, an effective daily amount of EPO was found to be 10 Units/kg for from 15 to 40 days. See Eshbach et al., *J. Clin. Invest.*, 74: 434 (1984).

The active EPO may be administered by any route appropriate to the condition being treated. Preferably, the EPO is injected into the bloodstream of the mammel being treated. It will be readily appreciated by those skilled in the art that the preferred route will vary with the condition being treated.

While it is possible for the active EPO to be administered as the pure or substantially pure compound, it is preferable to present it as a pharmaceutical formulation or preparation.

The formulations of the present invention, both for veterinary and for human use, comprise an active EPO protein, as above described, together with one or more pharmaceutically acceptable carriers therefor and optionally other therapeutic ingredients. The carrier(s) must be "acceptable" in the sense of being compatible with the other ingredients of the formulation and not deleterious to the recipient thereof. Desirably the formulation should not include oxidizing agents and other substances with which peptides are known to be incompatible. The formulations may conveniently be presented in unit dosage form and may be prepared by any of the methods well known in the art of pharmacy. All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for perenteral administration conveniently comprise sterile aqueous solutions of the active ingredient with solutions which are preferably isotonic with the blood of the recipient. Such formulations may be conveniently prepared by dissolving solid active ingredient in water to produce an aqueous solution, and rendering said solution sterile may be presented in unit or multi-dose containers, for example sealed ampoules or vials.

The term "EPO protein" includes the 1-methionine derivative of EPO protein (Met-EPO) and allelic variations of EPO protein. The mature EPO protein illustrated by SEQ ID NO:1 begins with the sequence Ala.-Pro.Pro.Arg . . . the beginning of which is depicted by the number "1" in SEQ ID NO:1. The Met-EPO would begin with the sequence Met.Ala.Pro.Pro.Arg . . .

The following examples are provided to aid in the understanding of the present invention, the true scope of which is set forth in the appended claims. It is understood that modifications can be made in the procedures set forth, without departing from the spirit of the invention. All temperatures are expressed in degrees Celsius and are uncorrected. The symbol for micron or micro, e.g., microliter, micromole, etc., is "u", e.g., ul, um, etc.

EXAMPLE 1

Purification of Erythropoietin

Crude erythropoientin preparations were concentrated by dialysis and proteolytic enzymes deactivated when necesary by heat treatment of 80° C. for 5 minutes. The crude preparation concentrates were then purified by the method described by Miyake et al., (1977) supra (the disclosure of which is hereby incorporated by reference) as follows.

A. Ethanol Precipitation

Batches containing about 100,000 IU of EPO activity at concentations of about 50 to 100 IU per absorbance unit at 280 nm were diluted to 50 ml with phosphate buffered solution (PBS) at 4° C. 12.5 ml of 10 M LiCl were added. Absolute ethanol 62.5 ml) at 4° was added slowly with stirring, which was continued for 30 min. after the addition was complete. After the flocculent precipitate had been allowed to settle for 10 min. it was removed by centrifugation at 21,000×g for 10 min at −15°. The pellet was washed three times with 10 ml of 50% ethanol, 1 M LiCl and the supernatants were pooled. The washed precipitate was dissolved in 20 ml of PBS, yielding a turbid solution (50% precipitate).

Sixty-seven milliliters of absolute ethanol were added slowly to the combined supernatants: stirring was continued for 30 min. and settling for 15 min. The precipitate was collected as before and washed twice with 10 ml of 65% ethanol, 0.7 M LiCl and the supernatants were pooled. The washed precipitate was dissolved in 20 ml of PBS (65% precipitate).

The the pooled supernatants, 96 ml of ethanol were added slowly and stirring was continued for 30 min. after which the precipitate was allowed to settle for 14 hr. at 4°. The precipitate was washed twice with 10 ml of 75% ethanol, 0.5 M LiCl, the supernatants were pooled, and the precipitate was dissolved in 20 ml of PBS (75% precipitate).

The combined supernatant was brought to 90% ethanol by addition of 540 ml of absolute alcohol, stirred for 30 min. and stored at −20° for 48 hr. before the precipitate was collected, dissolved in 50 ml of cold water and immediately frozen.

B. DEAE—Agarose Fractionation

The solution, in water, of a 90% ethanol precipitate was concentrated to about 5 ml on an Amicon UM-10 ultrafilter, then brought to 25 ml with 0.01 M Tris, pH 7.0, and a 50- ul aliquot was removed. The DEAE-agarose, 100 to 200 mesh, was degassed under reduced pressure, suspended in 0.01 M Tris, pH 7.0, and packed into a column 9.2×2.5 cm in diameter (bed volume, 45 ml). The gel was washed with 1.5 liters of 0.01 M Tris, pH 6.9; the ratio of absorbance units added to bed volume (ml) was 6.65. The sample was added to the column over a period of 40 min. and 150-drop fractions were collected. the column was washed with 211 ml of 0.01 M Tris, pH 7, and then eluted with the following buffers: 366 ml of 0.01 M Tris, pH 7.0; 5 mM $CaCl_2$, 270 ml of 0.01 Tris, pH 7.0; 17 mM $CaCl_2$; 194 ml of 0.01 M Tris, pH 7.0; 3 mM $CaCl_2$; and 65 ml of 0.1 M $CaCl_2$.

From this point on in the fractionation calcium was added to all buffers except those used with hydroxylapatite columns because there were inconsistent results and appreciable losses of activity when buffers without calcium were used. For the next step in purification, eluates from DEAE agarose columns were selected that had significant quantities of EPO activity.

C. Sulfopropyl-Sephadex Chromatography

The eluates (17 mM $CaCl_2$) from DEAE-agarose columns were desalted and concentrated on a UM-10 ultrafilter and then dialyzed against 2 liters of 5 mM $CaCl_2$. pH 7.5 overnight. In the sample run described below, 30 ml of dialyzed solution were brought to pH 4.50 by dropwise addition of 0.1 M HCl: the small amount of precipitate formed was removed by centrifugation and washed with 5 ml of 5 mM $CaCl_2$, pH 4.5. The wash, pooled with the supernatant, was applied to a sulfopropyl-Sephadex column (15.0×2.5 cm in diameter, bed volume, 78.3 ml) which had been equilibrated with 5 mM $CaCl_2$, pH 4.50. The absorbance units to bed volume (ml) ratio was 2.47. A low value for this ratio is preferred for optimal fractionation on sulfopropyl-Sephadex: for example, if the absorbance unit to bed volume ratio was greater than 10, almost all of the activity was found in the effluent fraction. The following buffers were used in developing the column. Input was: 5 mM calcium acetate, pH 4.50, specific conductivity = 1.075 umho $cm^{-1}$. Eluting buffers were: 7.5 mM calcium acetate, pH 4.70, specific conductivity 1,500 umho $cm^{-1}$: 15 mM calcium acetate, pH 5.25, specific conductivity = 2,100 umho $cm^{-1}$: 15 mM calcium acetate, 0.01 m Tris, pH 7.24, specific conductivity = 11,500 umho $cm^{-1}$. the column was run at 0.4 ml/min. at 4°, and 200-drop fractions were collected. After a reading was taken at 280 nm and the appropriate pools were made, the solutions were neutralized (within 1 hr. after elution) and aliquots were removed for assay and stored at −20°.

D. Gel Filtration

The 12.5 and 15 mM calcium acetate eluates from the sulfopropyl-Sephadex column separations were run in two separate batches on the same gel column. The pools were concentrated on Amicon UM-2 ultrafilters to about 5 ml and equilibrated with 10 mM $CaCl_2$, 10 mM Tris, pH 6.87, before application to the column. The Sephadex G-100 gel was degassed under reduced pressure and equilibrated with the same buffer before the column was poured. The column (100×2.5 cm diameter) was calibrated with markers of known molecular size before being used for the erythropooietin fractions. The void volume was 135 ml; bovine serum albumin monomer eluted at 224 ml. ovalbumin at 258 ml, and cytochrome at 368 ml. The sample was added to the bottom of the column, as was the buffer which was passed through the column at 21 to 22 ml by means of a Mariotte bottle with a 42 cm hydrostatic head. Each fraction collected was 4.1 ml (120 drops), and pools were made. The pools were concentrated by ultrafiltration and aliquots were assayed.

E. Hydroxylapatite Chromatography

Hydroxylapatite was packed under unit gravity into a column (6.1×1.5 cm diameter) and washed with 500 ml of water and then with 400 ml of 0.5 mM phosphate buffer, pH 7.1, conductivity = 69 umno $cm^{-1}$ (Buffer I), by use of a peristaltic pump which maintained the flow at 0.3 ml/min. After the buffer wash, the length of the column was 3.4 cm and the bed volume was 6.0 ml. the input sample was concentrated and desalted on an Amicon DM-5 ultrafilter by adding water to the concentrate and the wash of the filter were centrifuged at 6,000×g for 20 min. at 4°. The small insoluble pellet was washed once with 0.5 mM phosphate, pH 7.1, and the wash was added to the supernatant. An aliquot for assay was removed and the remainder (22 ml) was added to the column. The ratio of absorbance units added to bed volume (ml) was 1.82. The input buffer was pumped through the column until the effluent A was less than 0.005 (149 ml) and the following elution schedule was carried out: Buffer II, 1 mM phosphate (pH 7.1, specific conductivity 131=umho cm$^{-1}$, 150 ml (Fraction II)); Buffer III, 2 mM phosphate (ph 6.9, specific conductivity=270 umho cm$^{-1}$, 220 ml (fractions IIIA and IIIB)); Buffer IV, 3 mM phosphate (ph 6.9, specific conductivity=402 umho cm$^{1}$, 84 ml (Fraction IV)); Buffer V, 0.1 M phosphate (pH 6.8, specific conductivity=9.6 umho cm$^{-1}$, 134 ml (Fraction V)).

Fractions containing EPO were concentrated by means of Amicon DM-5 ultrafilter, an aliquot assayed and the concentrate stored frozen. The assay indicated a specific EPO activity of 83,000 IU per absorbance unit at 280 mm.

F. Reverse Phase HPLC

When analyzed by sodium dodecyl sulfate polyacrylamide gel electrophoresis (SDS PAGE) according to Laemmli, U.K., Nature, 15:Vol. 22, No. 259 pp. 680–685 (1970) this material from the hydroxylapatite column revealed several polypeptide components ranging from approximately 70,000 MW to 30,000 MW with the major component at about 34,000 MW. This partially pure preparation of EPO which was obtained in volumes of up to 10 ml in 10 mM phosphate buffer pH 7.0 was subjected to RPHPLC as described below.

The EPO preparation was concentrated 10-fold by partial lyophilization. Approximately 200 microliters of this concentrated material was injected onto a C-4 Vydac R-P HPLC column (25×0.45 cm, the Separations Group) and fractionated by reverse phase HPCL using the gradient conditions described in Table 1. Protein peaks were detected by UV absorption at 280 nm. A typical elution profile of this fractionation process is shown in FIG. 1. The identity of EPO was confirmed by SDS PAGE and N-terminal amino acid sequence analysis of the various peaks observed after R-P HPLC. The peak that is underlined in FIG. 1 (19) elutes coincidentally with a reading of 53% B on the gradient maker (Beckman Instruments, model 421). This material runs as a single band of about 34,000 MW using SDS PAGE and yields a single amino terminal sequence of: Ala, Pro, Pro, Arg, Leu, Ile, Cys - as has been previously reported for human EPO. Only this R-P HPLC fraction of about 34,000 MW showed any significant biological activity in vitro. The EPO protein eluted by R-PHPLC is about twice as pure as the material eluted from the hydroxylapatite column (STEP E).

TABLE 1

| Pump A 0.1% Trifluoracetic Acid (TFA) in water Pump B 95% Acetonitrile in 0.1% TFA in water | | |
|---|---|---|
| Gradient Time (min.) | % B | Duration |
| 0 | 0 | 2 |
| 2 | 25 | 3 |
| 5 | 100 | 75 |
| 90 | 0 | 3 |
| 100 | Reinject | |

Flow 1 ml/min.

EPO is quantified by either the 3H-thymidine assay (Krystal, Exp. Hematol. 11:649-60 (1983)) or CFU-E assay (Bersch et al., In vitro Aspects of Erythropoiesis, M.J. Murphy (Ed.), New York: Springer-Verloz 1978)

EXAMPLE 2

Purification of EPO

COS-cell conditioned media (121) with EPO concentrations up to 200ug/liter was concentrated to 600 ml using 10,000 molecular weight cutoff ultrafiltration membranes, such as a Millipore Pellican fitted with 5 sq. ft. of membrane. During the purification steps, immunologically active EPO was quantified by radioimmunoassay as described by Sherwood and Goldwasser, Blood 54:885-93 (1979). The antibody was provided by Dr. Judith Sherwood. The iodinated tracer was prepared from the homogeneous EPO produced in Example 1. The sensitivity of the assay is approximately 1 ng/ml. The retentate from the ultrafiltration was diafiltered against 4 ml. of 10 mM sodium phosphate buffered at pH 7.0. The concentrated and diafiltered conditioned media contained 2.5 mg of EPO in 380 mg of total protein. The EPO solution was further concentrated to 186 ml and the precipitated proteins were removed by centriguation at 110,000×g for 30 minutes.

The supernatant which contained EPO (2.0 mg) was adjusted to pH 5.5 with 50% acetic acid, allowed to stir at 4° C. for 30 minutes and the precipitate removed by centrifugation (at 13,000×g for 30 min.).

Carbonylmethyl Sepharose Chromatography

The supernatant from the centrifugation (20 ml) containing 200 μg of EPO (24 mg total protein) was applied to a column packed with CM-Sepharose (20 ml) equilibratred in 10 mM sodium acetate pH 5.5, washed with 40 ml of the same buffer. EPO which bound to the CM-Sepharose was eluted with a 100 ml gradient of NaO(0-1) in 10 mM sodium phosphate pH 5.5. The fractions containing EPO (total of 50 μg in 2 mg of total proteins) were pooled and concentrated to 2 ml using Amicon YM10 ultrafiltration membrane.

Reverse Phase-HPLC

The concentrated fractions from CM-Sepharose containing the EPO was further purified by reverse phase-HPLC using Vydac C-4 column. The EPO was applied onto the column equilibrated in 10% solvent B (Solvent A was 0.1% $CF_3CO_2H$ in water; solvent B was 0.1% $CF_3CO_2H$ in $CF_3CN$) at flow rate of 1 ml/min. The column was washed with 10% B for 10 minutes and the EPO was eluted with a linear gradient of B (10–70% in 60 minutes). The fractions containing EPO were pooled (~40 μg of EPO in 120 μg of total proteins) and lyophilized. The lyophilized EPO was reconstituted in 0.1M Tris-CHl at pH 7.5 containing 0.15M NaCl and rechromatographed on the reverse phase HPLC. The fractions containing the EPO were pooled and analyzed by SDS-polyacrylamide (10%) gel electrophoresis (Laemmli, U.K., supra). The pooled fractions of EPO contained 15.5 μg of EPO in 25 μg of total protein.

This invention has been described in detail including the preferred embodiments thereof. However, it will be appreciated that those skilled in the art, upon consideration of this disclosure, may make modifications and improvements within the scope of this invention.

What is claimed is:

1. A pharmaceutical composition for stimulating production of red blood cells comprising a therapeutically effective amount of homogeneous human EPO protein characterized by a molecular weight of about 34,000 daltons in a single band on SDS PAGE and movement as a single peak in reverse phase high performance liquid chromatography and a pharmaceutically acceptable vehicle.

2. A pharmaceutical composition for stimulating production of red blood cells comprising a therapeutically effective amount of homogeneous human EPO protein prepared by subjecting partially purified EPO having an in vivo specific activity of at least 80,000 IU per absorbance unit at 280 nanometers to reverse phase high performance liquid chromatography and eluting therefrom human EPO protein which has a molecular weight of about 34,000 daltons in a single band on SDS PAGE and movement as a single peak in reverse phase high performance liquid chromatography, and a pharmaceutically acceptable vehicle.

3. A method of treating a patient suffering from anemia to stimulate production of red blood cells, said method comprising administering to said patient a pharmaceutical composition according to claim 1 or 2.

4. The pharmaceutical composition of claim 1 wherein said EPO protein has the N-terminal partial amino acid sequence Ala, Pro, Pro, Arg, Leu, Ile, Cys.

5. The pharmaceutical composition of claim 1 or 4 wherein said EPO protein is derived from a urinary source.

6. The pharmaceutical composition of claim 2 wherein said EPO protein has the N-terminal partial amino acid sequence Ala, Pro, Pro, Arg, Leu, Ile, Cys.

7. The pharmaceutical composition of claim 2 or 6 wherein said EPO protein is derived from a urinary source.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 193 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:1:

```
Met  Gly  Val  His  Glu  Cys  Pro  Ala  Trp  Leu  Trp  Leu  Leu  Leu  Ser  Leu
-27

Leu  Ser  Leu  Pro  Leu  Gly  Leu  Pro  Val  Leu  Gly  Ala  Pro  Pro  Arg  Leu
                                                       1

Ile  Cys  Asp  Ser  Arg  Val  Leu  Glu  Arg  Tyr  Leu  Leu  Glu  Ala  Lys  Glu
               10                                                  20

Ala  Glu  Asn  Ile  Thr  Thr  Gly  Cys  Ala  Glu  His  Cys  Ser  Leu  Asn  Glu
                                        30

Asn  Ile  Thr  Val  Pro  Asp  Thr  Lys  Val  Asn  Phe  Tyr  Ala  Trp  Lys  Arg
          40                                            50

Met  Glu  Val  Gly  Gln  Gln  Ala  Val  Glu  Val  Trp  Gln  Gly  Leu  Ala  Leu
                              60

Leu  Ser  Glu  Ala  Val  Leu  Arg  Gly  Gln  Ala  Leu  Leu  Val  Asn  Ser  Ser
70                                                 80

Gln  Pro  Trp  Glu  Pro  Leu  Gln  Leu  His  Val  Asp  Lys  Ala  Val  Ser  Gly
                    90                                              100

Leu  Arg  Ser  Leu  Thr  Thr  Leu  Leu  Arg  Ala  Leu  Gly  Ala  Gln  Lys  Glu
                                   110

Ala  Ile  Ser  Pro  Pro  Asp  Ala  Ala  Ser  Ala  Ala  Pro  Leu  Arg  Thr  Ile
          120                                            130

Thr  Ala  Asp  Thr  Phe  Arg  Lys  Leu  Phe  Arg  Val  Tyr  Ser  Asn  Phe  Leu
                              140

Arg  Gly  Lys  Leu  Lys  Leu  Tyr  Thr  Gly  Glu  Ala  Cys  Arg  Thr  Gly  Asp
150                                              160

Arg
```